United States Patent [19]
Borowski et al.

[11] Patent Number: 4,541,954
[45] Date of Patent: Sep. 17, 1985

[54] METHOD FOR PREPARING 6-CHLORO-N-METHYL-2,3,4,5-TETRAHYDRO-1H-3-BENZAZEPINE

[75] Inventors: Stanley J. Borowski, West Chester; Thomas A. Post, Malvern, both of Pa.

[73] Assignee: SmithKline Beckman Corporation, Philadelphia, Pa.

[21] Appl. No.: 647,552

[22] Filed: Sep. 5, 1984

[51] Int. Cl.$^4$ .......................................... C07D 223/16
[52] U.S. Cl. ............................. 260/239 BB; 564/336
[58] Field of Search ................. 260/239 BB; 564/336

[56] References Cited

U.S. PATENT DOCUMENTS 4,200,754  4/1980  Holden et al. ...................... 546/141
4,251,660  2/1981  Lam et al. ............................ 546/150

FOREIGN PATENT DOCUMENTS 1118688  7/1968  United Kingdom ......... 260/239 BB

*Primary Examiner*—Glennon H. Hollrah
*Assistant Examiner*—D. B. Springer
*Attorney, Agent, or Firm*—Joseph A. Marlino; Stuart R. Suter; Alan D. Lourie

[57] ABSTRACT

A novel process for preparing 6-chloro-N-methyl-2,3,4,5-tetrahydro-1H-3-benzazepine comprising cyclizing N-methyl-N-[2-(2'-chlorophenyl)ethyl]-2-chloroethylamine hydrochloride in a solution of trichlorobenzene and aluminum chloride.

4 Claims, No Drawings

METHOD FOR PREPARING 6-CHLORO-N-METHYL-2,3,4,5-TETRAHYDRO-1H-3-BENZAZEPINE

This invention relates to a novel process for preparing 6-chloro-N-methyl-2,3,4,5-tetrahydro-1H-3-benzazepine. This compound has been disclosed as having utility as an alpha$_2$ antagonist, a pharmacological action which is associated with a broad spectrum of beneficial cardiovascular activity. The compound is particularly useful as an antihypertensive agent. (U.S. Pat. No. 4,465,677)

BACKGROUND OF THE INVENTION

In the above noted patent the title compound is prepared by cyclizing N-methyl-N-[2-(2'-chlorophenyl)-ethyl]-2-chloroethylamine hydrochloride under Friedel-Crafts conditions. The cyclization step is carried out using Lewis acids such as aluminum chloride in a melt of ammonium chloride.

U.S. Pat. Nos. 4,251,660 and 4,200,754 disclose a method of preparing tetrahydroisoquinolines. Both of these patents employ aluminum chloride as the cyclization agent. The U.S. Pat. No. 4,251,660 patent teaches that the reaction is done in the absence of an organic solvent. The U.S. Pat. No. 4,200,754 patent discloses that the reaction is done with conventional Friedel Crafts solvents, i.e., methylene chloride, tetrachloroethylene or dichloroethane. Other well known solvents employed during the Friedel Crafts reaction are nitrobenzene or decalin.

The above methods which employ either the conventional solvents or a melt in the process all proved commercially unsatisfactory when used in an attempt to prepare 6-chloro-N-methyl-2,3,4,5-tetrahydro-1H-3-benzazepine. These prior art methods resulted in very poor yields, from relatively no yield to about 25%, with the production of undesired isomers and other impurities.

In addition to the above conventional Friedel-Crafts solvents, chlorinated organic solvents such as monochloro and dichlorobenzene have been attempted with resultant low yields.

DESCRIPTION OF THE INVENTION

The novel process of this invention, which uses trichlorobenzene as the solvent, is unexpected in view of the prior art. The process selectively produces the desired 6-chloro isomer in greater than 90% yields. There is little isomerization, such as formation of the 7-chloro isomer. Unlike the conventional Friedel-Crafts solvents which result in decomposition to liquid and solid black masses, there is no decomposition and near quantitative yields when trichlorobenzene is employed. The process is clean and is readily adaptable to commercial scale. Further, the process is cost effective and the yield is up dramatically as compared to prior art methods.

The chemical method of this invention is represented by the following reaction.

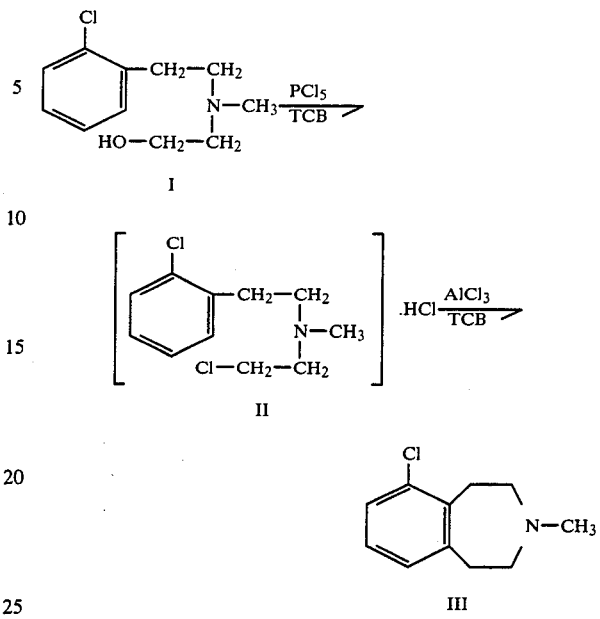

According to the above method, N-methyl-N-[2-(2'-chlorophenyl)ethyl]-2-hydroxyethyl-amine (Formula I) is chlorinated with a chlorinating agent, such as, phosphorous pentachloride in trichlorobenzene and converted to N-methyl-N-[2-(2'-chlorophenyl)ethyl]-2-chloroethylamine hydrochloride (Formula II) in situ. This is not isolated but converted directly to the N-methyl-6-chlorobenzazepine hydrochloride (Formula III) by the addition of aluminum chloride to the reaction mix. The rection is carried out at a temperature of from about 180° C. to about 215° C. (refluxing temperature) for a period of from about 3 to 8 hours, depending on conditions such as temperature, pressure, and concentration of aluminum chloride. The application of pressure permits a higher concentration of aluminum chloride thereby decreasing reaction time considerably, more than four fold. Advantageously, the pressure is greater than two atmospheres. The free base obtained from the hydrochloride salt after treatment with aqueous alkali is purified by distillation followed by conversion to the hydrochloride and recrystallization from methanol-ethyl acetate.

The reaction mixture is conveniently and optionally worked up by methods known to the art. Most commonly this involves quenching the reaction mixture, removal of the aluminum salts followed by extraction and purification of the final product.

The method of this invention is successfully carried out employing the isomers of trichlorobenzene, for example, the reaction progresses as expected if the 1,2,4; 1,2,3; to 1,3,5 isomer of trichlorobenzene or mixtures of them is used as the solvent. Advantageously, technical grade 1,2,4 isomer is employed because it has the lowest melting point (17° C.) and thus the greatest liquid working range.

The cyclization agent is aluminum chloride which forms a Friedel-Crafts complex which in turn cyclizes to form the desired product. Stoichiometric quantities of aluminum chloride may be used. In practice from about 2.4 to 3 mole equivalents of aluminum chloride compared to the starting material (Formula I) are employed. Excess amounts of aluminum chloride are not detrimental to the reaction.

The following example illustrates the process of this invention but is not to be construed as a limitation thereof.

EXAMPLE

A mixture of 121 l of 1,2,4-trichlorobenzene and 19.5 Kg. (75.0 m) of N-methyl-N-[2-(2'-chlorophenyl)ethyl]-2-hydroxyethylamine was agitated at a temperature of 20–30° C. and a homogenous solution was obtained. Phosphorous pentachloride, 7.2 Kg. (34.6 m) was added and the temperature was brought to 110° C.

To the above solution, containing N-methyl-N-[2-(2'-chlorophenyl)ethyl]-2-chloroethylamine hydrochloride, was slowly added 24.4 Kg. (18.3 m) of aluminum chloride while the temperature was maintained between 95° and 110° C. The reaction was then brought to a reflux temperature of 205° C. for six hours.

The reaction was quenched over a 2 hour period by cooling to 80° C. with an acidic aqueous mixture (450 l of H$_2$O, 18 l of HCl) with agitation. The quench was allowed to settle and the trichlorobenzene layer was separated.

The aqueous quench was layered with toluene (120 l) and the two phase mixture was brought to a pH of at least 11 with 50% aqueous sodium hydroxide.

The aqueous phase was extracted with toluene (120 ml) and the phase separated. The aqueous wash was discarded and the toluene phase was fractionally distilled. After removal of the toluene, the distillate at 134° to 143° C. pot temperature and 126° to 140° C. vapor temperature at 15 to 20 torr was collected and resulted in a 91% yield of 6-chloro-3-methyl-2,3,4,5-tetrahydro-1H-3-benzazepine as the free base.

The above oily base in toluene was treated with anhydrous hydrogen chloride, then recrystallized from methanol/ethyl acetate yielded 6-chloro-3-methyl-2,3,4,5-tetrahydro-1H-3-benzazepine hydrochloride, m.p. 268–270° C. (d).

What is claimed is:

1. In the method of preparing 6-chloro-N-methyl-2,3,4,5-tetrahydro-1H-3-benzazepine comprising the step of reacting N-methyl-N-[2-(2'-chlorophenyl)ethyl]-2-chloroethylamine in the presence of a solution of an aluminum chloride catalyst, the improvement comprising using trichlorobenzene as the solvent.

2. The method of claim 1 in which 1,2,4-trichlorobenzene is used.

3. The method of claim 1 in which the reaction is carried out at a temperature of from about 180° C. to about 215° C. for from about 3 to about 8 hours.

4. The method of claim 1 in which the chloroethylamine is prepared by reacting N-methyl-N-[2-(2'-chlorophenyl)ethyl]-2-hydroxyethylamine with phosphorous pentachloride in trichlorobenzene.

* * * * *